United States Patent [19]
Harrington et al.

[11] Patent Number: 5,856,576
[45] Date of Patent: Jan. 5, 1999

[54] ARYNE INTERMEDIATES AND A PROCESS FOR THE PREPARATION THEREOF

[75] Inventors: Philip M. Harrington, Pennington; Kenneth A. M. Kremer, Lawrenceville, both of N.J.

[73] Assignee: American Cyanamid Company, Madison, N.J.

[21] Appl. No.: 15,817

[22] Filed: Jan. 29, 1998

Related U.S. Application Data

[60] Provisional application No. 60/037,129 Feb. 4, 1997.
[51] Int. Cl.$^6$ .................................................. C07C 209/74
[52] U.S. Cl. ........................ 564/305; 544/211; 564/404; 564/407; 564/443; 564/442; 568/322; 568/323; 568/705
[58] Field of Search ..................... 564/305, 404, 564/407, 443, 442; 544/211; 568/705, 322, 323

[56] References Cited

U.S. PATENT DOCUMENTS

| | | |
|---|---|---|
| 3,562,277 | 2/1971 | Hansen et al. . |
| 4,075,346 | 2/1978 | Sasajima et al. . |
| 4,622,065 | 11/1986 | Van Gemert . |
| 4,988,695 | 1/1991 | Brown et al. . |
| 5,009,699 | 4/1991 | Brady et al. . |
| 5,107,023 | 4/1992 | Brady et al. . |
| 5,281,726 | 1/1994 | Cortes . |
| 5,362,911 | 11/1994 | Cevasco . |
| 5,364,968 | 11/1994 | Burello et al. . |
| 5,405,998 | 4/1995 | Cevasco . |
| 5,414,136 | 5/1995 | Cortes . |

FOREIGN PATENT DOCUMENTS

| | | |
|---|---|---|
| 0 380 257 | 1/1990 | European Pat. Off. . |
| 0 604 705 A1 | 5/1993 | European Pat. Off. . |
| 661 276 A1 | 10/1994 | European Pat. Off. . |
| 1 527 783 | 7/1976 | United Kingdom . |
| 1 545 341 | 2/1977 | United Kingdom . |
| 2 281 296 | 1/1995 | United Kingdom . |
| WO 95/29167 A1 | 11/1995 | WIPO . |
| WO 95/29902 | 11/1995 | WIPO . |

OTHER PUBLICATIONS

Rudisill, D.E. and Stille, J.K., "Palladium–catalysed synthesis of 2–substituted indoles" Journal of Organic Chemistry, vol. 54, No. 25, 1989, pp. 5856–5866.

Stephens, R.D. and Castro, E.C., Journal of Organic Chemistry, 1963, 28, pp. 3313–3315.

Sonogashira, K.; Tohda, Y. and Hagihara, N., Tetrahedron Letters, No. 50, pp. 4467–4470 (1975).

Chapdelaine, M.J.; Warwick, P.J. and Shaw, A. Journal of Organic Chemistry, 1989, 54, pp. 1218–1221.

Takahashi, S.; Kuroyama, Y.; Sonogashira, K. and Hagihara, N., Synthesis, vol. 8, pp. 627–630 (1980).

*Primary Examiner*—Brian M. Burn
*Attorney, Agent, or Firm*—Barbara L. Renda

[57] ABSTRACT

There are provided aryne intermediates of formula I, useful in the manufacture of herbicidal compounds.

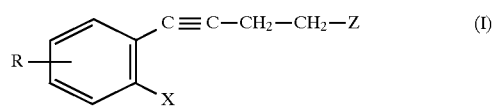

Also provided is a method to prepare the formula I intermediates via the palladium catalyzed coupling of an o-halonitrobenzene or o-haloaniline with 3-butyne-1-ol.

23 Claims, No Drawings

ARYNE INTERMEDIATES AND A PROCESS FOR THE PREPARATION THEREOF

BACKGROUND OF THE INVENTION

This Application claims the benefit of U.S. Provisional application Ser. No. 60/037,129, filed Feb. 4, 1997.

Herbicidal sulfamoyl urea compounds are described in WO 95/29902, EP 661,276, WO 95/29167 and U.S. Pat. No. 4,622,065. A particularly potent and highly cereal selective sulfamoyl urea herbicidal agent is the subject of U.S. Pat. No. 5,009,699. This agent is especially useful for the selective control of a variety of weed species in the presence of cereal crops and particularly for controlling broadleaf weeds and sedges in the presence of transplanted or paddy rice. Therefore, alternate, effective, cost-efficient methods of manufacture of herbicidal sulfamoyl ureas, and particularly cereal-selective sulfamoyl ureas, are of continued interest.

Certain key intermediates in the manufacture of the above-said herbicides and the cereal-selective herbicide, 1-{[o-(cyclopropylcarbonyl)phenyl]sulfamoyl}-3-(4,6-dimethoxy-2-pyrimidinyl)urea, such as o-aminophenyl cyclopropyl ketone, o-nitrophenyl cyclopropyl ketone, 4-halo-o-nitrobutyrophenone, and 4-halo-o-aminobutyrophenone are described in U.S. Pat. Nos. 5,362,911; 5,364,968; 5,405,998 and 5,414,136. However, alternate and effective methods to prepare these key intermediate alkyl and cycloalkyl phenyl ketones and their derivatives from readily available, non-toxic starting materials are still being sought.

Therefore, it is an object of this invention to provide aryne compounds useful to prepare substituted and unsubstituted 4-hydroxy-(o-substituted phenyl)butyrophenone intermediate compounds.

It is another object of this invention to provide a process to prepare said aryne compounds from readily available, relatively non-toxic starting materials.

It is a further object of this invention to provide an alternate process for the manufacture of key intermediates useful in the manufacture of sulfamoyl urea herbicidal agents and sulfamoyl urea, cereal-selective, herbicidal agents.

It is a feature of this invention that the preparative methods allow for the use of readily available, relatively non-toxic and cost-efficient starting materials.

Other objects and features of the invention will become apparent from the detailed description thereof set forth hereinbelow.

SUMMARY OF THE INVENTION

The present invention provides aryne compounds of formula I

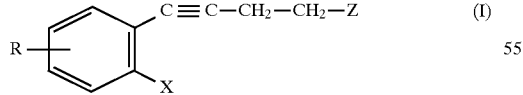

wherein R is H, CN, F, formyl, $C_1$–$C_4$alkyl optionally substituted with one or more halogen, $C_1$–$C_3$alkoxy, $C_1$–$C_3$alkylthio, $C_1$–$C_3$alkylsulfinyl or $C_1$–$C_3$alkylsulfonyl groups,
$C_1$–$C_4$alkoxy optionally substituted with one or more halogen, $C_1$–$C_3$alkoxy, $C_1$–$C_3$alkylthio, $C_1$–$C_3$-alkylsufinyl or $C_1$–$C_3$alkylsulfonyl groups,
$C_1$–$C_4$alkylthio optionally substituted with one or more halogen, $C_1$–$C_3$alkoxy, $C_1$–$C_3$alkylthio, $C_1$–$C_3$-alkylsufinyl or $C_1$–$C_3$alkylsulfonyl groups,
$C_1$–$C_4$alkylsulfinyl optionally substituted with one or more halogen, $C_1$–$C_3$alkoxy, $C_1$–$C_3$alkylthio, $C_1$–$C_3$-alkylsufinyl or $C_1$–$C_3$alkylsulfonyl groups,
$C_1$–$C_4$alkylsulfonyl optionally substituted with one or more halogen, $C_1$–$C_3$alkoxy, $C_1$–$C_3$alkylthio, $C_1$–$C_3$-alkylsufinyl or $C_1$–$C_3$alkylsulfonyl groups,
$C_1$–$C_4$alkylcarbonyl optionally substituted with one or more halogen, $C_1$–$C_3$alkoxy, $C_1$–$C_3$alkylthio, $C_1$–$C_3$-alkylsufinyl or $C_1$–$C_3$alkylsulfonyl groups,
$C_1$–$C_4$alkoxycarbonyl optionally substituted by one or more halogen or $C_1$–$C_3$alkoxy groups,
di($C_1$–$C_4$alkyl)amino optionally substituted by one or more halogen or $C_1$–$C_3$alkoxy groups,
di($C_1$–$C_4$alkyl)aminocarbonyl optionally substituted by one or more halogen or $C_1$–$C_3$alkoxy groups,
di($C_1$–$C_4$alkyl)aminosulfonyl optionally substituted by one or more halogen or $C_1$–$C_3$alkoxy groups, or
a heterocyclic ring having 2 to 6 carbon atoms and 1 to 3 nitrogen, oxygen or sulfur atoms and being optionally substituted on the carbon atoms with one or more fluorine, $C_1$–$C_4$alkyl or $C_1$–$C_4$haloalkyl groups;
X is $NO_2$ or $NR_1R_2$;
Z is OH, Br, Cl or $OSO_2R_3$;
$R_1$ and $R_2$ are each independently hydrogen, formyl, acetyl, haloacetyl, $CO_2R_4$ or benzyl optionally substituted on the aromatic ring with one to three fluorine, nitro, $C_1$–$C_3$alkyl or $C_1$–$C_3$alkoxy groups; and
$R_3$ and $R_4$ are each independently $C_1$–$C_6$alkyl, $C_1$–$C_6$haloalkyl or phenyl optionally substituted with one to three fluorine, nitro, $C_1$–$C_3$alkyl or $C_1$–$C_3$alkoxy groups; or
when X is $NR_1R_2$, the acid addition salts thereof.

Also provided is a method to prepare the formula I compounds via the palladium catalyzed coupling of an o-halonitrobenzene or o-haloaniline with 3-butyne-1-ol.

The formula I aryne compounds are useful as intermediates in the manufacture of sulfamoyl urea herbicidal agents.

DETAILED DESCRIPTION OF THE INVENTION

Sulfamoyl urea derivatives are useful as herbicidal agents, in particular, 1-{[o-(cyclopropylcarbonyl)phenyl]sulfamoyl}-3-(4,6-dimethoxy-2-pyrimidinyl)urea is a potent, environmentally benign herbicide with important cereal crop selectivity. A key intermediate in the manufacture of this particular herbicide is 1-(o-anilino)-4-halo-1-butanone. This key intermediate may be obtained from the corresponding o-nitrobenzene precursor or alternatively from the 4-hydroxy-anilino- or 4-hydroxy-nitrobenzene-1-butanone precursors.

It has now been found that aryne compounds of formula I

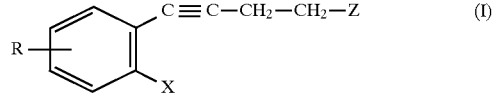

wherein R is H, $NH_2$, CN, $NO_2$, F, formyl, $C_1$–$C_4$alkyl optionally substituted with one or more halogen, $C_1$–$C_3$alkoxy, $C_1$–$C_3$alkylthio, $C_1$–$C_3$alkylsulfinyl or $C_1$–$C_3$alkylsulfonyl groups,
$C_1$–$C_4$alkoxy optionally substituted with one or more halogen, $C_1$–$C_3$alkoxy, $C_1$–$C_3$alkylthio, $C_1$–$C_3$-alkylsufinyl or $C_1$–$C_3$alkylsulfonyl groups,
$C_1$–$C_4$alkylthio optionally substituted with one or more halogen, $C_1$–$C_3$alkoxy, $C_1$–$C_3$alkylthio, $C_1$–$C_3$-alkylsufinyl or $C_1$–$C_3$alkylsulfonyl groups, $C_1$–$C_4$alkylsulfinyl optionally substituted with one or more halogen, $C_1$–$C_3$alkoxy, $C_1$–$C_3$alkylthio, $C_1$–$C_3$-alkylsufinyl or $C_1$–$C_3$alkylsulfonyl groups, $C_1$–$C_4$alkylsulfonyl optionally substituted with one or more halogen, $C_1$–$C_3$alkoxy, $C_1$–$C_3$alkylthio, $C_1$–$C_3$-alkylsufinyl or $C_1$–$C_3$alkylsulfonyl groups, $C_1$–$C_4$alkylcarbonyl optionally substituted with one or more halogen, $C_1$–$C_3$alkoxy, $C_1$–$C_3$alkylthio, $C_1$–$C_3$-alkylsufinyl or $C_1$–$C_3$alkylsulfonyl groups, $C_1$–$C_4$alkoxycarbonyl optionally substituted by one or more halogen or $C_1$–$C_3$alkoxy groups, di($C_1$–$C_4$alkyl)amino optionally substituted by one or more halogen or $C_1$–$C_3$alkoxy groups, di($C_1$–$C_4$alkyl)aminocarbonyl optionally substituted by one or more halogen or $C_1$–$C_3$alkoxy groups, di($C_1$–$C_4$alkyl)aminosulfonyl optionally substituted by one or more halogen or $C_1$–$C_3$alkoxy groups, or a heterocyclic ring having 2 to 6 carbon atoms and 1 to 3 nitrogen, oxygen or sulfur atoms and being optionally substituted on the carbon atoms with one or more fluorine, $C_1$–$C_4$alkyl or $C_1$–$C_4$haloalkyl groups;

X is $NO_2$ or $NR_1R_2$;

Z is OH, Br, Cl or $OSO_2R_3$;

$R_1$ and $R_2$ are each independently hydrogen, formyl, acetyl, haloacetyl, $CO_2R_4$ or benzyl optionally substituted on the aromatic ring with one to three fluorine, nitro, $C_1$–$C_3$alkyl or $C_1$–$C_3$alkoxy groups; and $R_3$ and $R_4$ are each independently $C_1$–$C_6$alkyl, $C_1$–$C_6$haloalkyl or phenyl optionally substituted with one to three fluorine, nitro, $C_1$–$C_3$alkyl or $C_1$–$C_3$alkoxy groups; or when X is $NR_1R_2$, the acid addition salts thereof are useful in the preparation of important 4-halo or 4-hydroxy-o-substituted benzene-butanone intermediates in the manufacture of sulfamoyl urea herbicides.

The term haloacetyl designates an acetyl group substituted by one to three halogen atoms which may be the same or different. The term halogen as used in this definition of haloacetyl designates Cl, Br, I or F.

Preferred compounds of formula I are those compounds wherein R is H; Z is OH; and $R_1$ and $R_2$ are each independently H.

Advantageously, the aryne compounds of formula I may be prepared from readily available, non-toxic starting materials such as o-halobenzenes of formula III, preferably o-iodobenzenes or o-bromobenzenes and alkynes of formula IV, preferably 3-butyne-1-ol. In accordance with the method of invention, a formula III o-halobenzene, preferably o-iodoaniline or o-bromoaniline, may be reacted with at least one molar equivalent of a formula IV alkyne, preferably 3-butyne-1-ol, in the presence of a catalytically effective amount of a palladium(II) catalyst and a copper(I) catalyst and in the presence of an organic amine. The reaction is illustrated in flow diagram I wherein Hal is I, Cl or Br and R, X and Z are defined hereinabove.

Flow Diagram I

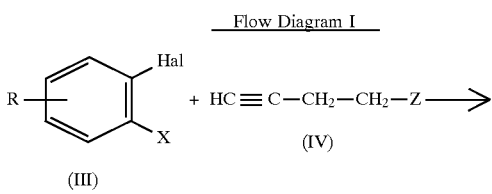

(IV)

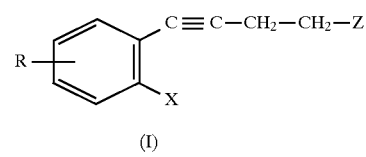

(I)

Organic amines suitable for use in the method of invention are any of those commonly used in manufacturing procedures such as triethylamine, diethylamine, tributylamine, diisopropylamine, and the like, preferably triethylamine.

Palladium catalysts may be any known catalyst wherein the palladium metal is present with a valence of two, such as bis(triphenylphosphine)palladium(II)chloride, palladium(II)acetate, palladium(II)chloride, and the like, preferably bis(triphenylphosphine)palladium(II)chloride. Similarly, the copper catalyst may be any known catalyst wherein the copper metal is present with a valence of one such as a copper(I)halide, preferably copper(I)iodide.

Conveniently the aryne compounds of the invention may be readily converted to key 4-halo or 4-hydroxy-o-substituted benzene-butanone intermediates essential in the manufacture of sulfamoyl urea herbicidal agents. In one embodiment of the invention, compounds of formula I wherein Z is hydroxy may be converted to the desired 4-hydroxyphenyl butanones of formula II in a single hydration step or, preferably, the desired formula II compound may be prepared in a single contiguous or continuous process.

In accordance with one embodiment of the inventive process, an o-halobenzene of formula III may be reacted with at least one molar equivalent of 3-butyne-1-ol in the presence of a catalytically effective amount of a palladium(II) catalyst and copper(I)catalyst and in the presence of an organic amine to give an aryne intermediate of formula Ia and the formula Ia intermediate may be hydrated with a hydrating agent and water, optionally at an elevated temperature, to give the desired formula II compound. The reaction sequence is shown in flow diagram II wherein Hal designates I, Cl or Br and R and X are as described hereinabove for formula I.

Flow Diagram II

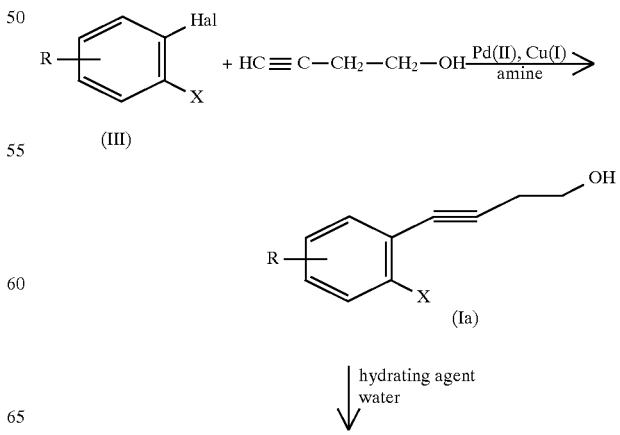

-continued
Flow Diagram II

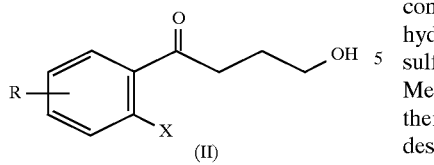

Hydrating agents suitable for use may be those commonly known in the art such as HgO, $H_2SO_4$; $Na_2S$, HCl; and the like.

Although the inventive process may be practiced at room temperature, it is understood that increased temperatures may decrease reaction time. However, excessively high temperatures may have adverse effects such as decomposition of reactants or products or facilitation of undesired side reactions. Suitable reaction temperatures range from about 0° C. to 110° C., preferably about 25° C. to 90° C.

The compound of formula II may be converted to the corresponding cyclopropyl ketone by displacing the hydroxy moiety with halogen, for example, by reacting the formula II butanone with a hydrogen halide to form the corresponding 4-halobutanone of formula V and dehydrohalogenating the resultant halobutanone to give the desired cyclopropyl product of formula VI. The reaction sequence is shown in flow diagram III.

Flow Diagram III

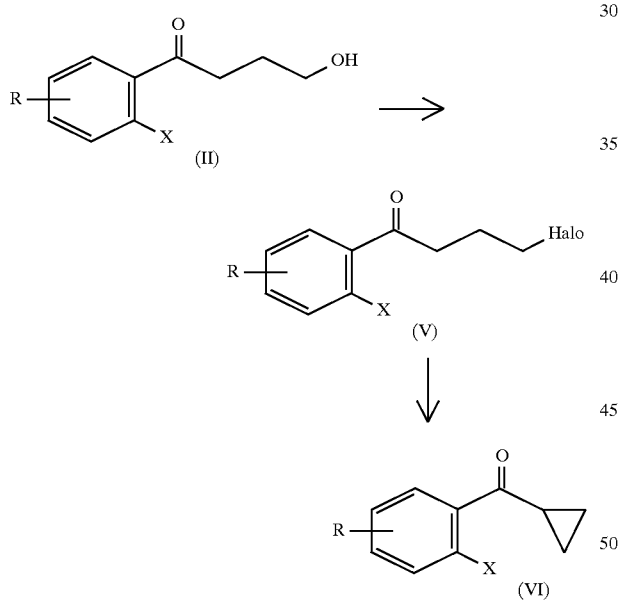

Methods to convert compounds of formula V wherein R is hydrogen to corresponding compounds of formula VI are described in U.S. Pat. No. 5,362,911. Methods to convert the formula VI cyclopropyl ketone wherein R is hydrogen and X is $NH_2$ to a cereal-selective, herbicidal, sulfamoyl urea are described in U.S. Pat. No. 5,008,699. Similarly, methods to convert the formula VI cyclopropyl ketone wherein R is hydrogen and X is $NO_2$ to a cereal-selective, herbicidal, sulfamoyl urea are described in U.S. Pat. No. 5,364,968. Methods to convert general phenyl ketones of formula V to their corresponding sulfamoyl urea herbicidal products are described in WO 95/29902, EP 661,276, WO 95/29167 and U.S. Pat. No. 4,622,065.

In accordance with another embodiment of the invention the halobenzene of formula III may be reacted with 3-butyne-1-ol in the presence of a catalytically effective amount of a palladium(II) catalyst and a copper(I) catalyst and in the presence of an organic amine to form the aryne intermediate of formula Ia. The formula Ia aryne may then be hydrated with hydrating agent to form the 4-hydroxyphenylbutanone of formula II. The formula II butanone may be halogenated with a hydrogen halide to give the corresponding 4-halo compound of formula V, which may then be dehydrohalogenated to give the cyclopropyl phenyl ketone of formula VI. When the formula VI compound is the compound wherein X is $NH_2$, said compound may be reacted with a 2-aminoaryl compound of formula VIII and chlorosulfonyl isocyanate in the presence of triethylamine and a solvent to give the desired herbicidal product of formula VII. The reaction sequence is shown in flow diagram IV wherein Halo designates Cl, Br, I or F; A is N or $CR_6$;

$R_5$ is H, halogen, $C_1-C_4$alkyl optionally substituted with one or more halogen or $C_1-C_3$alkoxy groups,
  $C_1-C_4$alkoxy optionally substituted with one or more halogen or $C_1-C_3$alkoxy groups,
  $C_1-C_4$alkylthio optionally substituted with one or more halogen or $C_1-C_3$alkoxy groups,
  $C_1-C_4$alkylsulfinyl optionally substituted with one or more halogen or $C_1-C_3$alkoxy groups,
  $C_1-C_4$alkylsulfonyl optionally substituted with one or more halogen or $C_1-C_3$alkoxy groups, or
  $C_1-C_4$alkylamino or di($C_1-C_4$alkyl)amino each alkyl group being optionally substituted with one or more halogen or $C_1-C_3$alkoxy groups;

$R_6$ is H or halogen; and $R_7$ is hydrogen, $C_1-C_4$alkyl optionally substituted with one or more halogen or $C_1-C_3$alkoxy groups,
  $C_1-C_4$alkoxy optionally substituted with one or more halogen or $C_1-C_3$alkoxy groups,
  $C_1-C_4$alkylthio optionally substituted with one or more halogen or $C_1-C_3$alkoxy groups,
  $C_1-C_4$alkylsulfinyl optionally substituted with one or more halogen or $C_1-C_3$alkoxy groups,
  $C_1-C_4$alkylsulfonyl optionally substituted with one or more halogen or $C_1-C_3$alkoxy groups, or
  $C_1-C_4$alkylamino or di($C_1-C_4$alkyl)amino each alkyl group being optionally substituted with one or more halogen or $C_1-C_3$alkoxy group.

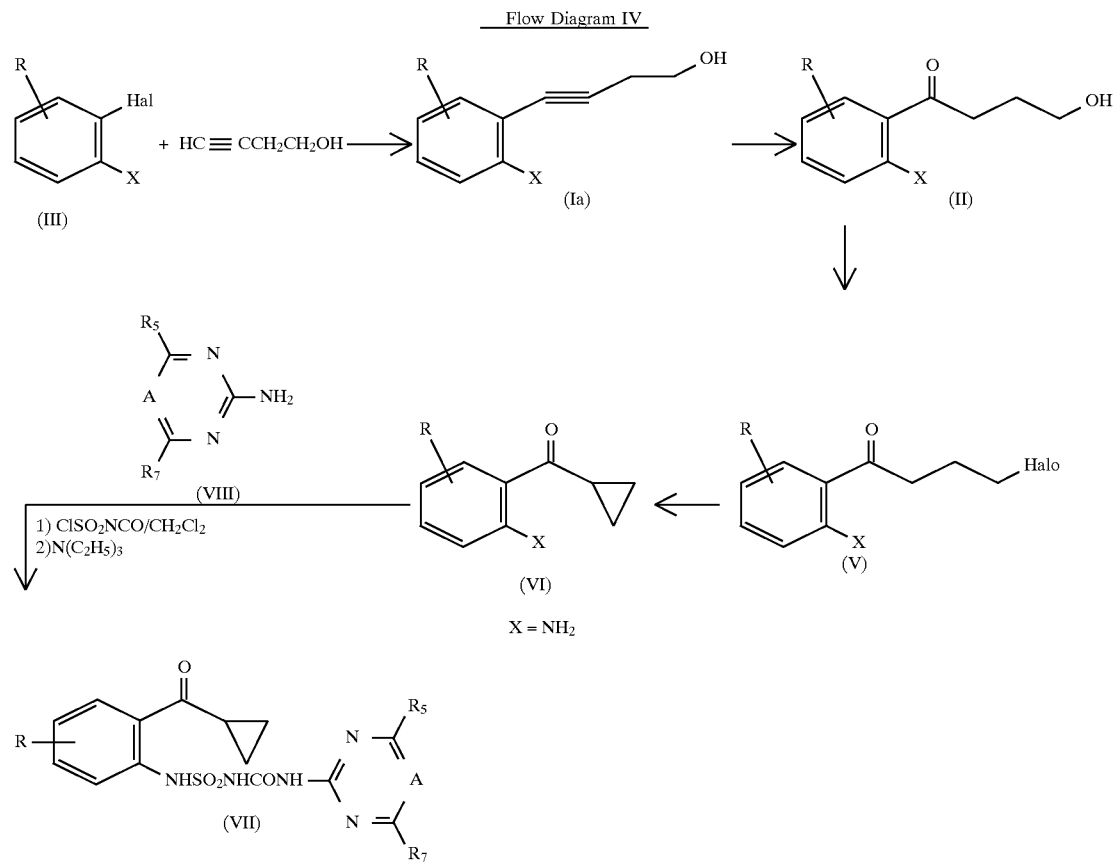

It is understood that compounds of formula II, V or VI wherein X is $NO_2$ or $NR_1R_2$ and either or both of $R_1R_2$ is other than hydrogen, may be converted to the corresponding aniline analogues by catalytic reduction or hydrolysis techniques, respectively. For example, when X is $NO_2$ for a compound of formula II, V or VI, said compound may be reduced with hydrogen gas in the presence of a catalyst optionally in the presence of a solvent to give the corresponding compound of formula II, V or VI wherein X is $NH_2$. Similarly, using known hydrolysis methods, a compound of formula II, V or VI wherein X is $NR_1R_2$ and either one or both of $R_1$ and $R_2$ are other than hydrogen may be hydrolyzed to give the corresponding compound of formula II, V or VI wherein X is $NH_2$.

For a more clear understanding of the invention, the following examples are set forth below. These examples are merely illustrative and are not understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

The term NMR designates nuclear magnetic resonance.

EXAMPLE 1

Preparation of 4-(o-anilino)-3-butyne-1-ol

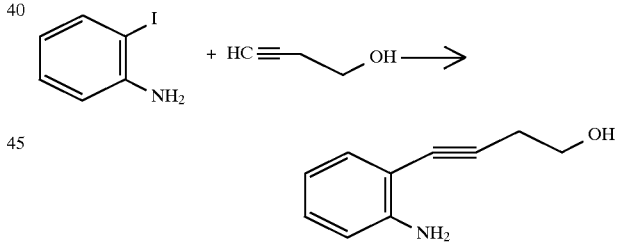

A solution of o-iodoaniline (35.0 g, 0.16 mol) in 640 ml of triethylamine, under nitrogen, is treated sequentially with bis(triphenylphosphine)palladium(II)chloride (2.24 g, 0.0032 mol), 3-butyne-1-ol (16.8 g, 0.24 mol) and copper (I)iodide (0.3 g, 0.0016 mol), stirred for 4.5 hours and filtered. The filtercake is washed with toluene and the filtrates are combined and concentrated in vacuo to give a dark oil residue. The residue is dissolved in methylene chloride, washed with water and filtered through a silica gel pad. The filtrate is concentrated in vacuo to give the title product as a dark oil, 25.2 g, 98% yield, identified by NMR and mass spectral analyses.

EXAMPLE 2

Preparation of 4-(o-nitrophenyl)-3-butyne-1-ol

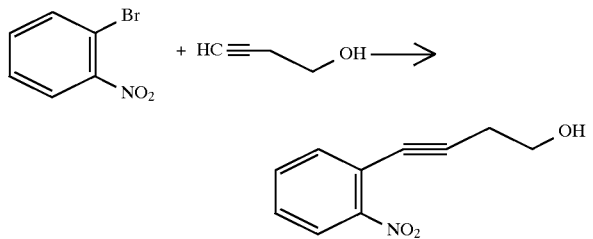

A solution of o-bromonitrobenzene (8.1 g, 0.04 mol) in 160 ml of triethylamine, under nitrogen, is treated sequentially with bis(triphenylphosphine)palladium(II)chloride (0.28 g, 0.4 mmol), 3-butyne-1-ol (2.81 g, 0.04 mol) and copper(I)iodide (0.15 g, 0.8 mmol), stirred for about 16 hours and filtered. The filtercake is washed with toluene. The filtrates are combined and concentrated in vacuo to give the title product as a dark oil, 6.0 g, 78.5% yield, identified by NMR and mass spectral analyses.

EXAMPLE 3

Preparation of 4-hydroxy-(o-anilino)-1-butanone

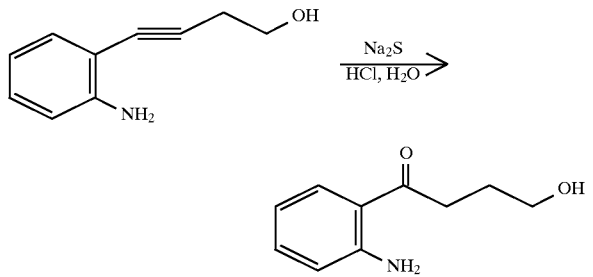

A solution of 4-(o-anilino)-3-butyne-1-ol (28 g, 90% pure, 0.155 mol) in 1.8 L methanol is treated sequentially with 1.35 kg of aqueous sodium sulfide (0.186 mol) and 176 g of dilute HCl (0.46 mol), heated at reflux for 9.4 hours, cooled to room temperature and filtered through celite. The filtrate is concentrated in vacuo and the concentrate is extracted with methylene chloride. The extracts are combined, washed with water and filtered through a silica gel pad. The filtrate is concentrated in vacuo to give the title product as a light orange solid, 16.6 g, 54.8% yield, identified by NMR and mass spectral analyses.

EXAMPLE 4

Preparation of 1-(o-anilino)-4-chloro-1-butanone hydrochloride

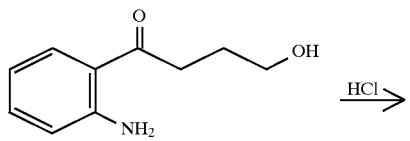

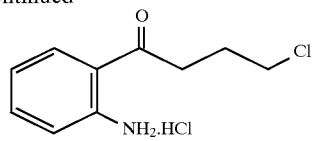

A mixture of 1-(o-anilino)-4-hydroxy-1-butanone (9.3 g, 5.1 mmol), 26 ml water and 90 ml of 37% HCl is heated at reflux temperature for 6.5 hours, cooled to room temperature and filtered. The filtercake is dried to give the title product as a white solid, 8.0 g. The filtrate is extracted with methylene chloride; the extracts are combined and the solvent evaporated in vacuo to give an additional 1.1 g of the title product, 73% overall yield, mp 142°–145° C., identified by NMR and mass spectral analyses.

EXAMPLE 5

Preparation of o-aminophenyl cyclopropyl ketone

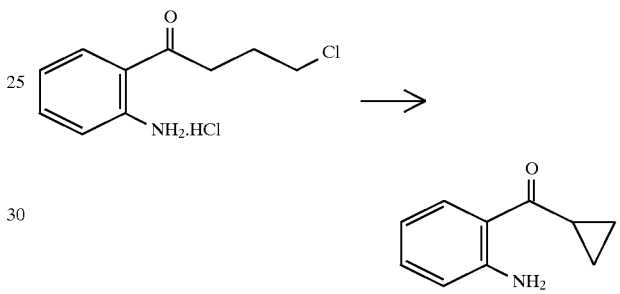

A solution of 1-(o-anilino)-4-chloro-1-butanone hydrochloride (0.3 g, 1.3 mmol) in a mixture of methylene chloride and ethylene dichloride is treated with 10% NaOH (1.2 g, 3.0 mmol) and 75% aqueous methyl tributylammonium chloride (0.05 g, 0.2 mmol), heated at 50° C. for 5 hours and cooled to room temperature. The phases are separated and the aqueous phase is extracted with methylene chloride. The organic extracts are combined, washed with water and concentrated in vacuo to give the title product as a white solid, 0.14 g, 70% yield, mp 46°–48° C., identified by NMR and mass spectral analyses.

EXAMPLE 6

Preparation of 1-(o-nitrophenyl)-4-hydroxy-1-butanone

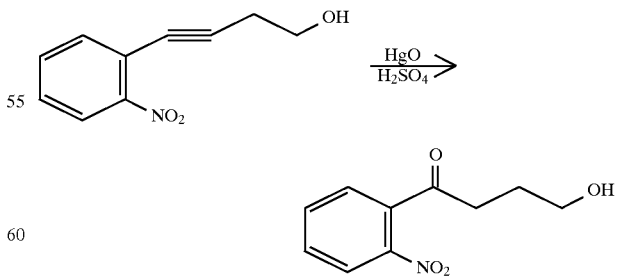

A mixture of HgO (0.21 g, 1.0 mmol) in 50 ml of 0.12N $H_2SO_4$ is heated to 60° C., treated dropwise with a solution of 4-(o-nitrophenyl)-3-butyne-1-ol (3.70 g, 19.4 mmol) in 25 ml of tetrahydrofuran over a 10 minute period, held at 60°

EXAMPLE 7

Preparation of 1-(o-nitrophenyl)-4-bromo-1-butanone

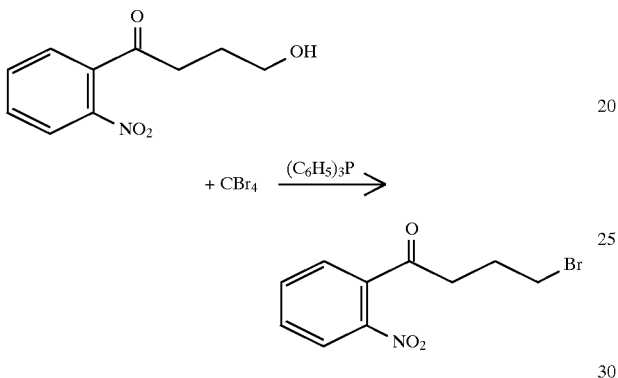

A mixture of 1-(o-nitrophenyl)-4-hydroxy-1-butanone (1.33 g, 6.4 mmol) and CBr$_4$ (2.32 g, 7.0 mmol) in toluene is treated with triphenylphospine (2.50 g, 9.5 mmol), heated at 60° C. with stirring under nitrogen for 24 hours, cooled to room temperature and poured onto water. The resultant aqueous mixture is extracted with ethyl acetate. The extracts are combined, washed with brine, dried over Na$_2$SO$_4$ and concentrated in vacuo to give a residue. The residue is purified by flash column chromatography (silica gel; gradient 1:4→1:2 ethyl acetate: hexanes as eluent) to give the title product as a brown oil, 0.90 g, 52% yield, identified by NMR and mass spectral analyses.

EXAMPLE 8

Preparation of o-nitrophenyl cyclopropyl ketone

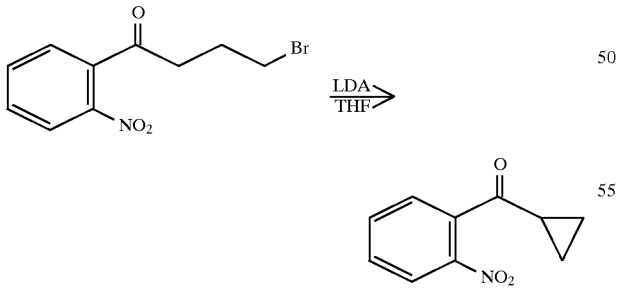

A solution of 1 (o-nitrophenyl)-4-bromo-1-butanone (0.75 g, 2.75 mmol) in dry tetrahydrofuran (THF) under nitrogen is cooled to −78° C. with stirring, cautiously treated with 2.21 ml of 1.5M lithium diisopropylamide (LDA) in cyclohexane (3.3 mmol LDA), held at −78° C. for 1 hour, allowed to warm to 0° C. for 2 hours and poured onto a saturated NH$_4$Cl solution. The resultant mixture is extracted C. for 3 hours, treated with additional HgO (0.84 g, 3.9 mmol) suspended in 25 ml of 0.12N H$_2$SO$_4$, held at 60° C. for 4 hours, cooled to room temperature and diluted with water. The resultant aqueous mixture is extracted with ether. The extracts are combined, washed with brine, dried over Na$_2$SO$_4$ and concentrated in vacuo to give a residue. The residue is purified by flash column chromatography (silica gel; gradient 1:1→2:1 ethyl acetate: hexanes as eluent) to give the title product as a brown oil, 1.48 g, 37% yield, identified by NMR and mass spectral analyses.

with ethyl acetate. The extracts are combined, washed with brine, dried over Na$_2$SO$_4$ and concentrated in vacuo to give a residue. The residue is purified by flash column chromatography (silica gel; gradient 15%→25% ethyl acetate in hexane as eluent) to give the title product as a yellow oil, 0.34 g, 64% yield, identified by NMR and mass spectral analyses.

I claim:

1. A compound of formula I

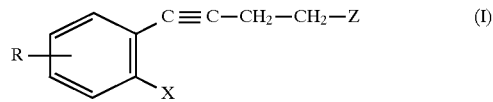

wherein R is H, CN, F, formyl, C$_1$-C$_4$alkyl optionally substituted with one or more halogen, C$_1$-C$_3$alkoxy, C$_1$-C$_3$alkylthio, C$_1$-C$_3$alkylsulfinyl or C$_1$-C$_3$alkylsulfonyl groups, C$_1$-C$_4$alkoxy optionally substituted with one or more halogen, C$_1$-C$_3$alkoxy, C$_1$-C$_3$alkylthio, C$_1$-C$_3$alkylsulfinyl or C$_1$-C$_3$alkylsulfonyl groups, C$_1$-C$_4$alkylthio optionally substituted with one or more halogen, C$_1$-C$_3$alkoxy, C$_1$-C$_3$alkylthio, C$_1$-C$_3$alkylsulfinyl or C$_1$-C$_3$alkylsulfonyl groups, C$_1$-C$_4$alkylsulfinyl optionally substituted with one or more halogen, C$_1$-C$_3$alkoxy, C$_1$-C$_3$alkylthio, C$_1$-C$_3$alkylsulfinyl or C$_1$-C$_3$alkylsulfonyl groups, C$_1$-C$_4$alkylsulfonyl optionally substituted with one or more halogen, C$_1$-C$_3$alkoxy, C$_1$-C$_3$alkylthio, C$_1$-C$_3$alkylsulfinyl or C$_1$-C$_3$alkylsulfonyl groups, C$_1$-C$_4$alkylcarbonyl optionally substituted with one or more halogen, C$_1$-C$_3$alkoxy, C$_1$-C$_3$alkylthio, C$_1$-C$_3$alkylsulfinyl or C$_1$-C$_3$alkylsulfonyl groups, C$_1$-C$_4$alkoxycarbonyl optionally substituted by one or more halogen or C$_1$-C$_3$alkoxy groups, di(C$_1$-C$_4$alkyl)amino optionally substituted by one or more halogen or C$_1$-C$_3$alkoxy groups, di(C$_1$-C$_4$alkyl)aminocarbonyl optionally substituted by one or more halogen or C$_1$-C$_3$alkoxy groups, di(C$_1$-C$_4$alkyl)aminosulfonyl optionally substituted by one or more halogen or C$_1$-C$_3$alkoxy groups, or a heterocyclic ring having 2 to 6 carbon atoms and 1 to 3 nitrogen, oxygen or sulfur atoms and being optionally substituted on the carbon atoms with one or more fluorine, C$_1$-C$_4$alkyl or C$_1$-C$_4$haloalkyl groups;

X is NO$_2$ or NR$_1$R$_2$;

Z is OH, Br, Cl or OSO$_2$R$_3$;

R$_1$ and R$_2$ are each independently hydrogen, formyl, acetyl, haloacetyl, CO$_2$R$_4$ or benzyl optionally substituted on the aromatic ring with one to three fluorine, nitro, C$_1$-C$_3$alkyl or C$_1$-C$_3$alkoxy groups; and R$_3$ and R$_4$ are each independently C$_1$-C$_6$alkyl, C$_1$-C$_6$haloalkyl or phenyl optionally substituted with one to three fluorine, nitro, C$_1$-C$_3$alkyl or C$_1$-C$_3$alkoxy groups; or when X is NR$_1$R$_2$, the acid addition salts thereof.

2. The compound according to claim 1 wherein R is H.
3. The compound according to claim 2 wherein X is NO$_2$.
4. The compound according to claim 2 wherein X is NH$_2$.
5. The compound according to claim 2 wherein Z is OH.
6. The compound according to claim 3 wherein Z is OH.
7. The compound according to claim 4 wherein Z is OH.

8. A process for the preparation of a compound of formula I

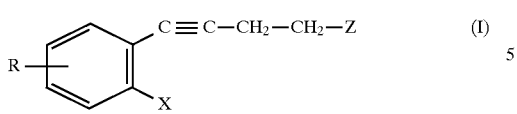

wherein R is defined in claim 1;
X is $NO_2$ or $NR_1R_2$;
Z is OH, Br, Cl or $OSO_2R_3$;

$R_1$ and $R_2$ are each independently hydrogen, formyl, acetyl, haloacetyl, $CO_2R_4$ or benzyl optionally substituted on the aromatic ring with one to three fluorine, nitro, $C_1$–$C_3$alkyl or $C_1$–$C_3$alkoxy groups; and $R_3$ and $R_4$ are each independently $C_1$–$C_6$alkyl, $C_1$–$C_6$haloalkyl or phenyl optionally substituted with one to three fluorine, nitro, $C_1$–$C_3$alkyl or $C_1$–$C_3$alkoxy groups which comprises reacting a halobenzene of formula III

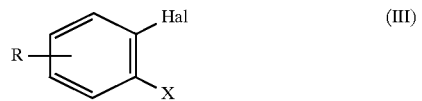

wherein Hal is Cl, I or Br and R and X are as defined for formula I with at least one molar equivalent of a butyne compound of formula IV $$HC \equiv C-CH_2-CH_2-Z \quad (IV)$$

wherein Z is as defined for formula I in the presence of a catalytically effective amount of a palladium(II)catalyst and a copper(I)catalyst and in the presence of an organic amine.

9. The process according to claim 8 wherein the palladium (II)catalyst is bis(triphenylphosphine)palladium(II)chloride and the copper(I)catalyst is copper(I)iodide.

10. The process according to claim 8 wherein the organic amine is triethylamine or diethylamine.

11. The process according to claim 8 having a formula III compound wherein R is H.

12. A process for the preparation of a compound of formula II

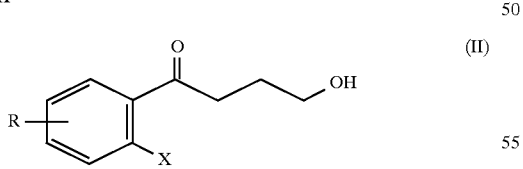

wherein R is defined in claim 1;
X is $NO_2$ or $NR_1R_2$;
$R_1$ and $R_2$ are each independently hydrogen, formyl, acetyl, haloacetyl, $CO_2R_4$ or benzyl optionally substituted on the aromatic ring with one to three fluorine, nitro, $C_1$–$C_3$alkyl or $C_1$–$C_3$alkoxy groups; and
$R_4$ is $C_1$–$C_6$alkyl, $C_1$–$C_6$haloalkyl or phenyl optionally substituted with one to three fluorine, nitro, $C_1$–$C_3$alkyl or $C_1$–$C_3$alkoxy groups which comprises reacting a compound of formula III

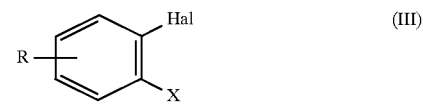

wherein X and R are as defined above and Hal is Cl, I or Br with at least one molar equivalent of 3-butyne-1-ol in the presence of a catalytically effective amount of a palladium(II)catalyst and a copper(I)catalyst and in the presence of an organic amine to give an intermediate of formula Ia

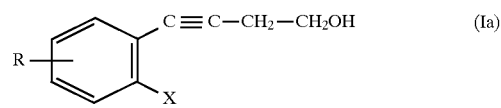

wherein R and X are defined above and hydrating the formula Ia intermediate in the presence of water and a hydrating agent to give the desired formula II compound.

13. The process according to claim 12 wherein the palladium(II)catalyst is bis(triphenylphosphine)palladium (II)chloride and the copper(I)catalyst is copper(I)iodide.

14. The process according to claim 12 wherein the organic amine is triethylamine or diethylamine.

15. The process according to claim 12 wherein the hydrating agent is HgO, $H_2SO_4$ or $Na_2S$, HCl.

16. The process according to claim 12 having a formula III compound wherein R is H and X is $NO_2$ or $NH_2$.

17. A process for the preparation of a compound of formula VII

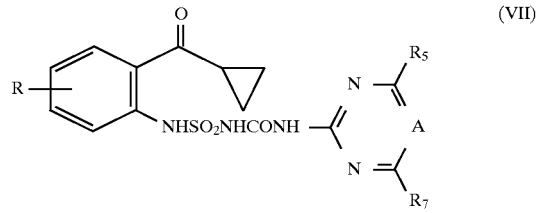

wherein R is defined in claim 1 and
A is N or $CR_6$;
$R_5$ is H, halogen, $C_1$–$C_4$alkyl optionally substituted with one or more halogen or $C_1$–$C_3$alkoxy groups,
$C_1$–$C_4$alkoxy optionally substituted with one or more halogen or $C_1$–$C_3$alkoxy groups,
$C_1$–$C_4$alkylthio optionally substituted with one or more halogen or $C_1$–$C_3$alkoxy groups,
$C_1$–$C_4$alkylsulfinyl optionally substituted with one or more halogen or $C_1$–$C_3$alkoxy groups,
$C_1$–$C_4$alkylsulfonyl optionally substituted with one or more halogen or $C_1$–$C_3$alkoxy groups, or
$C_1$–$C_4$alkylamino or di($C_1$–$C_4$alkyl)amino each alkyl group being optionally substituted with one or more halogen or $C_1$–$C_3$alkoxy groups;
$R_6$ is H or halogen; and
$R_7$ is hydrogen, $C_1$–$C_4$alkyl optionally substituted with one or more halogen or $C_1$–$C_3$alkoxy groups,
$C_1$–$C_4$alkoxy optionally substituted with one or more halogen or $C_1$–$C_3$alkoxy groups,
$C_1$–$C_4$alkylthio optionally substituted with one or more halogen or $C_1$–$C_3$alkoxy groups,
$C_1$–$C_4$alkylsulfinyl optionally substituted with one or more halogen or $C_1$–$C_3$alkoxy groups, $C_1$–$C_4$alkylsulfonyl optionally substituted with one or more halogen or $C_1$–$C_3$alkoxy groups, or $C_1$–$C_4$alkylamino or di($C_1$–$C_4$alkyl)amino each alkyl group being optionally substituted with one or more halogen or $C_1$–$C_3$alkoxy group which comprises the following steps:

a) reacting a halobenzene of formula III

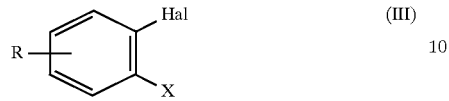

wherein R is defined in claim 1;

X is $NO_2$ or $NH_2$; and Hal is Cl, I or Br with at least one molar equivalent of 3-butyne-1-ol in the presence of a catalytically effective amount of a palladium(II)catalyst and a copper(I)catalyst and in the presence of an organic amine to form an aryne compound of formula Ia

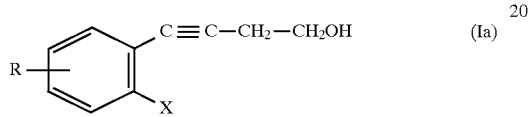

wherein R and X are defined hereinabove;

b) hydrating said formula I aryne with a hydrating agent to give a 4-hydroxy-(o-nitrophenyl)butanone or 4-hydroxy-o-aminophenyl)butanone of formula II

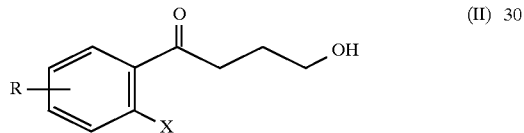

wherein R and X are defined hereinabove;

c) halogenating said 4-hydroxy-butanone with a hydrogen halide to give a 4-halo-butanone compound of formula V

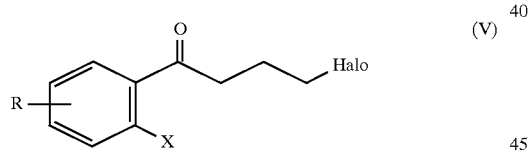

wherein R is defined above;

X is $NO_2$ or $NH_2$; and Halo is Cl, Br, I or F;

d) dehydrohalogenating said formula V compound in the presence of a base and a phase transfer catalyst and optionally in the presence of a solvent to form an o-nitrophenyl cyclopropyl ketone or o-aminophenyl cyclopropyl ketone of formula VI

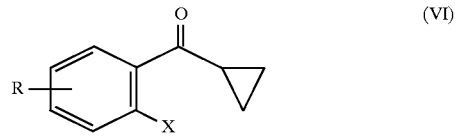

wherein R is defined above and X is $NH_2$ or $NO_2$;

e) when X is $NO_2$, reducing said o-nitrophenyl cyclopropyl ketone of formula VI in the presence of hydrogen and a catalyst optionally in the presence of a solvent to form the corresponding o-aminophenyl cyclopropyl ketone of formula VI wherein X is $NH_2$; and f) reacting said formula VI o-aminophenyl cyclopropyl ketone with a 2-aminoaryl compound of formula VIII

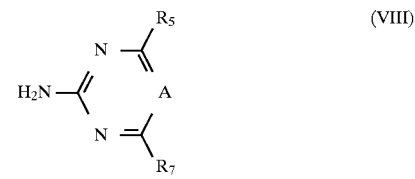

wherein A, $R_5$ and $R_7$ are defined above and chlorosulfonyl isocyanate in the presence of triethylamine and a solvent to give the desired sulfamoyl urea compound of formula VII.

18. The process according to claim 17 wherein the palladium(II)catalyst in step (a) is bis(triphenylphosphine)palladium(II)chloride.

19. The process according to claim 17 wherein the copper(I)catalyst is copper(I)iodide.

20. The process according to claim 17 wherein the organic amine in step (a) is triethylamine or diethylamine.

21. The process according to claim 17 wherein the hydrating agent in step (b) is HgO, $H_2SO_4$ or $Na_2S$, HCl.

22. The process according to claim 17 wherein the hydrogen halide in step (c) is hydrogen chloride or hydrogen bromide.

23. The process according to claim 17 for preparing a compound of formula VII wherein A is $CR_6$; R and $R_6$ are each H; and $R_5$ and $R_7$ are each methoxy.

* * * * *